(12) United States Patent
Fiferlick

(10) Patent No.: US 8,428,970 B1
(45) Date of Patent: Apr. 23, 2013

(54) INFORMATION RECORD MANAGEMENT SYSTEM

(76) Inventor: Jeffrey Fiferlick, Sioux Falls, SD (US)

( * ) Notice: Subject to any disclaimer, the term of this patent is extended or adjusted under 35 U.S.C. 154(b) by 151 days.

(21) Appl. No.: 13/181,775

(22) Filed: Jul. 13, 2011

(51) Int. Cl.
*G06Q 50/00* (2006.01)
*G06K 5/00* (2006.01)

(52) U.S. Cl.
USPC ............................................. 705/3; 235/380

(58) Field of Classification Search ............ 705/2–4, 705/26.5, 67; 235/380, 382, 492; 709/217, 709/228; 713/201, 202, 186
See application file for complete search history.

(56) References Cited

U.S. PATENT DOCUMENTS

| | | | |
|---|---|---|---|
| 6,523,009 B1 | 2/2003 | Wilkins | |
| 6,826,536 B1 | 11/2004 | Forman | |
| 6,898,299 B1 | 5/2005 | Brooks | |
| 7,181,017 B1 | 2/2007 | Nagel et al. | |
| 7,493,266 B2 | 2/2009 | Gupta | |
| 7,539,532 B2 | 5/2009 | Tran | |
| 7,539,533 B2 | 5/2009 | Tran | |
| 7,542,911 B2 | 6/2009 | Barret et al. | |
| 7,558,622 B2 * | 7/2009 | Tran | 600/509 |
| 7,578,438 B2 | 8/2009 | Hogg et al. | |
| 7,587,368 B2 | 9/2009 | Felsher | |
| 7,593,549 B2 | 9/2009 | Reiner | |
| 7,614,549 B2 | 11/2009 | Hogg et al. | |
| 7,617,972 B2 | 11/2009 | Hogg et al. | |
| 7,650,262 B2 | 1/2010 | Pearson et al. | |
| 7,694,887 B2 * | 4/2010 | Jones et al. | 235/492 |
| 7,698,154 B2 | 4/2010 | Marchosky | |
| 7,702,522 B1 | 4/2010 | Sholem | |
| 7,716,072 B1 | 5/2010 | Green, Jr. et al. | |
| 7,805,377 B2 | 9/2010 | Felsher | |
| 7,909,246 B2 | 3/2011 | Hogg et al. | |
| 2003/0217294 A1 * | 11/2003 | Kyle | 713/202 |
| 2004/0129787 A1 * | 7/2004 | Saito et al. | 235/492 |
| 2004/0172558 A1 * | 9/2004 | Callahan et al. | 713/201 |
| 2005/0091338 A1 * | 4/2005 | de la Huerga | 709/217 |
| 2006/0005041 A1 * | 1/2006 | Lazeroms et al. | 713/186 |
| 2006/0106852 A1 * | 5/2006 | Siddall et al. | 707/101 |
| 2006/0120571 A1 * | 6/2006 | Tu et al. | 382/118 |
| 2006/0219776 A1 * | 10/2006 | Finn | 235/380 |
| 2007/0116036 A1 | 5/2007 | Moore | |
| 2007/0117082 A1 * | 5/2007 | Winneg et al. | 434/350 |
| 2008/0082671 A1 * | 4/2008 | Meijer et al. | 709/228 |
| 2008/0120296 A1 | 5/2008 | Kariathungal et al. | |
| 2008/0172737 A1 | 7/2008 | Shen et al. | |
| 2008/0223926 A1 * | 9/2008 | Miller et al. | 235/382 |
| 2010/0205667 A1 * | 8/2010 | Anderson et al. | 726/19 |
| 2011/0153362 A1 * | 6/2011 | Valin et al. | 705/3 |

* cited by examiner

*Primary Examiner* — Lena Najarian
*Assistant Examiner* — Natalie A Pass
(74) *Attorney, Agent, or Firm* — Hagen, Wilka & Archer LLP; Mark A. Ekse

(57) ABSTRACT

A information record management system for providing record owner controlled access to medical records by authorized users and owners through secure communications channels. The information record management system includes a database having a plurality of user records from a plurality of record owners, an authentication channel to limit access to authorized users utilizing multiple authentication techniques including physical and biometric aspects, and providing streaming video representations of each user record for added security.

9 Claims, 3 Drawing Sheets

INFORMATION RECORD MANAGEMENT SYSTEM

BACKGROUND OF THE INVENTION

1. Field of the Invention

The present invention relates to electronic medical record systems and more particularly pertains to a new information record management system for providing record owner controlled access to medical records by authorized users and owners through secure communications channels.

2. Description of the Prior Art

The use of electronic medical records is known in the prior art. Many such systems have been commercial implemented and comprise standard technological building blocks. One such system is disclosed in U.S. Pat. No. 7,587,368 issued to David Paul Felsher on Sep. 8, 2009, which discloses and enables a system providing remote access to information records, the infrastructure associated with such a system, and multiple security and authentication steps utilized in such systems. The U.S. Pat. No. 7,587,368 is hereby incorporated by reference for all purposes.

Other illustrative examples include U.S. Pat. No. 6,523,009, and United States Patent Applications 2008/0172737 and 2008/0120296 which disclose a variety of electronic medical record systems. Many of these systems utilize proprietary formats and interfaces, and are specially adapted to give an institution control over the medical records.

The utility U.S. Pat. No. 6,523,009 does not include two layer security access including a physical element and a biometric element, secure transmission of patient information to approved providers on mobile devices using video transmission to provide additional security, patient access to their records on demand with some correction capabilities, limited access to qualified first responders and/or emergency room personnel with partial patient security information, and record search methodology for facilitating faster retrieval of currently pertinent information.

The published patent application 2008/0172737 does not provide for the two discrete security elements (physical and biometric), nor the first responder limited access based upon partial authentication.

Further, the published patent application 2008/0120296 does not include the routing of the data to handheld devices through secure video, the patent access and modification of the data, two element security, or first responder access based upon partial authentication.

In these respects, the information record management system according to the present invention substantially departs from the conventional concepts and designs of the prior art, and in so doing provides an apparatus primarily developed for the purpose of providing record owner controlled access to medical records by authorized users and owners through secure communications channels.

SUMMARY OF THE INVENTION

In view of the foregoing disadvantages inherent in the known types of electronic medical record systems now present in the prior art, the present invention provides a new information record management system construction wherein the same can be utilized for providing record owner controlled access to medical records by authorized users and owners through secure communications channels.

To attain this, the present invention generally comprises a database having a plurality of user records from a plurality of record owners, an authentication channel to limit access to authorized users utilizing multiple authentication techniques including physical and biometric aspects, and providing streaming video representations of each user record for added security.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The present invention builds on these known systems to provide specific benefits. One aspect of the present invention is the ability to present all records as streaming video without regard to the original format of the information record. While many systems may accommodate streaming video for some media types, the present invention provides care-givers access to any information record they are authorized to access as streaming video. This use of streaming video provides an additional layer of security by eliminating local copies on multiple devices.

Another aspect of the present invention is establishing a system where the record owner, often "the patient" has control of the information records. The owner is able to provide correction and updates to information such as address, insurance provider, pharmacist, living will, advanced directives and the like. When a medical person creates a record, that record is maintained in its original extent even if a corrective version is made by the user.

Still another aspect of the present invention is to allow for secure third party authentication of a care provider or institutional insurance coordinator to access an insurers preauthorization system.

Still another aspect of the invention is to provide a means for secured automatic logon to the institutional system by a care provider without the need for the care provider to enter information into the user terminal.

Yet another aspect of the present invention is to provide an automated translation of multiple medical codes and diagnosis into a set of instructions for the owner, in the owner's primary language such as English, Spanish, French, Chinese, American Sign Language, etc.

Even still another aspect of the present invention is the reduction in billing fraud by requiring authentication of the patient through the use of an encoded identification card along with biometric information of the patient prior to pre-authorization by the insurer.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein.

DESCRIPTION OF PREFERRED EMBODIMENTS

Figure 1:
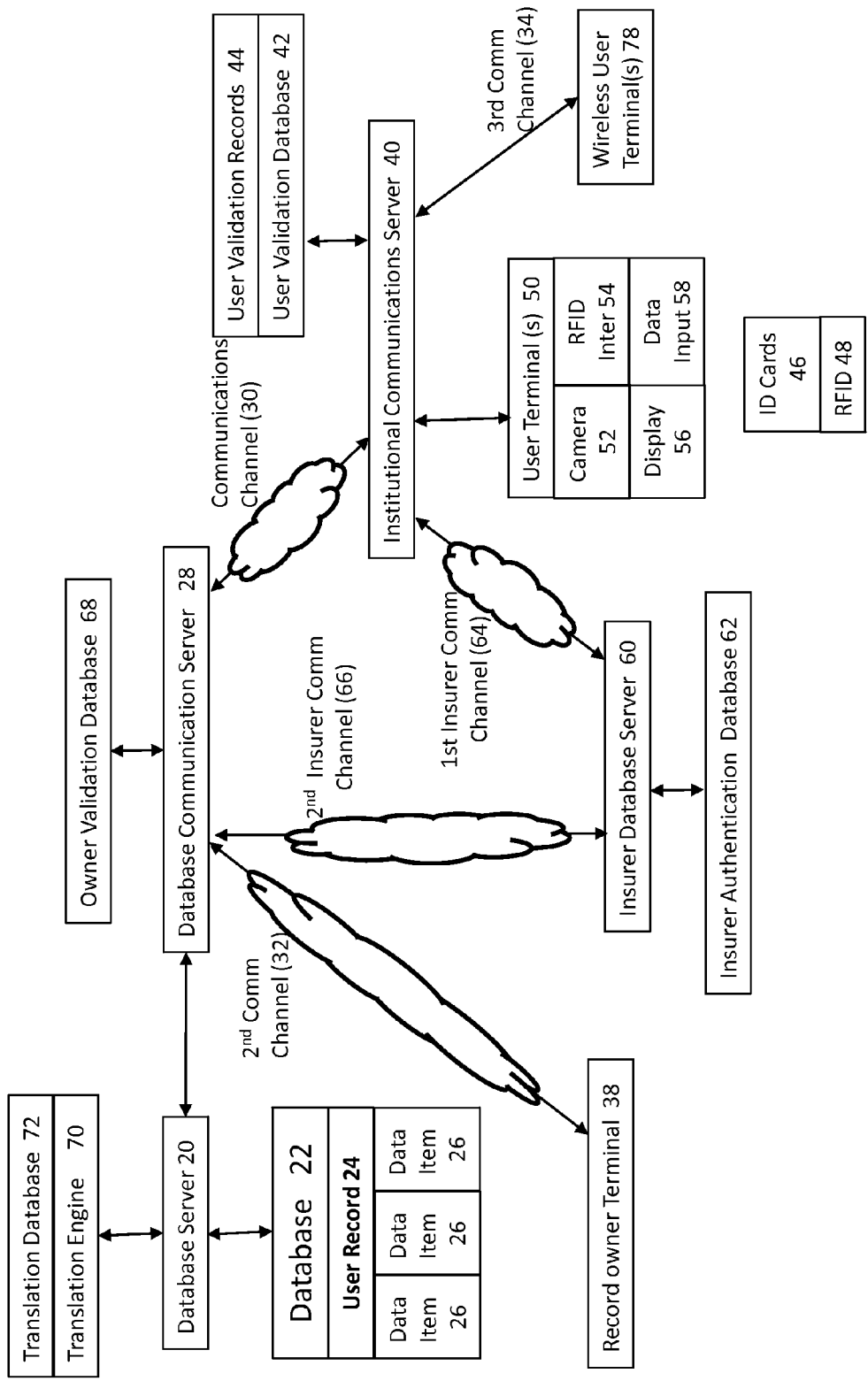
FIG. 1 is a schematic functional block diagram of a new information record management system according to the present invention.
Figure 2:
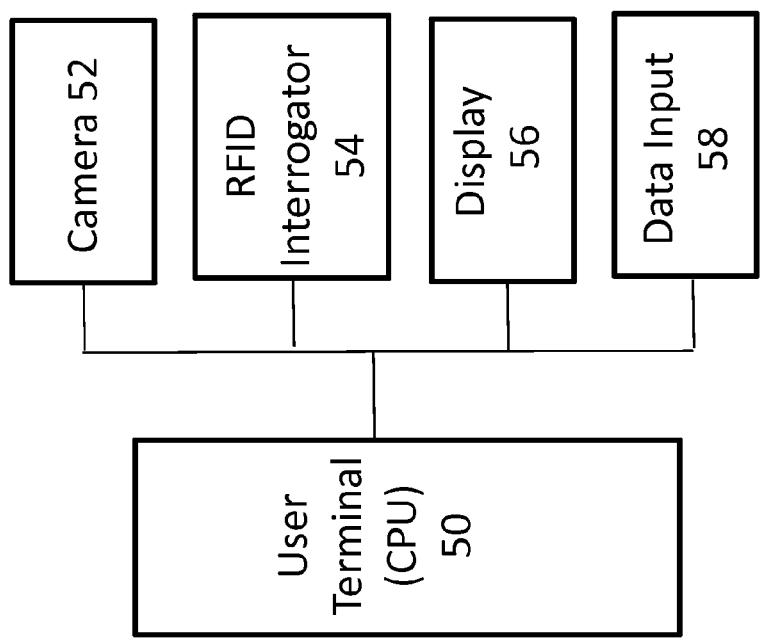
FIG. 2 is a schematic block diagram of a user terminal of the present invention.
Figure 3:
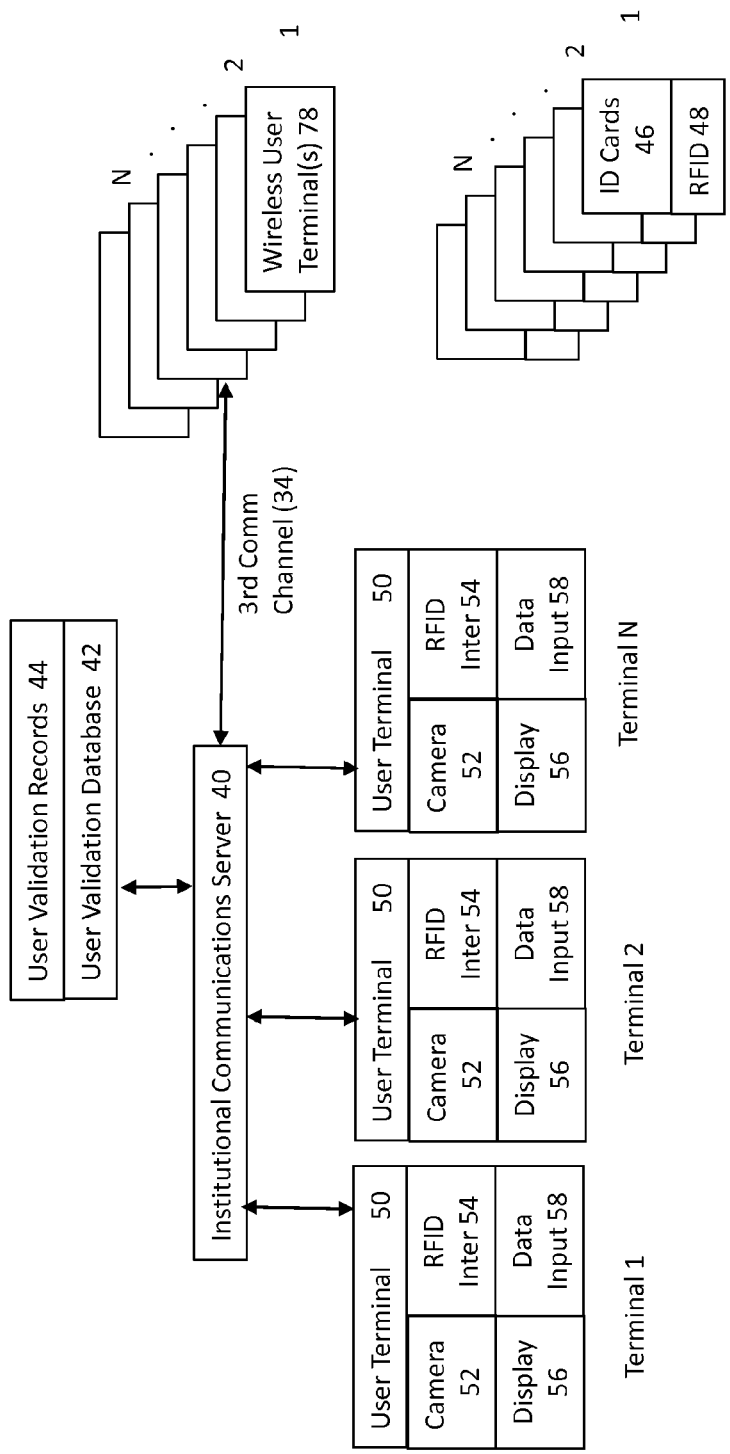
FIG. 3 is a schematic block diagram of an institutional installation of the present invention.

With reference now to the drawings, and in particular to FIGS. 1 through 3 thereof, a new information record management system embodying the principles and concepts of the present invention and generally designated by the reference numeral 10 will be described.

As best illustrated in FIGS. 1 through 3, the information record management system 10 generally comprises a database 22, a database communications server 28, at least one institutional communications server 40, a communications channel 30, at least one user terminal 50, and a user validation database 42.

The database 22 runs on at least one database server 20. Preferably, the database 22 is replicated on multiple geographically diverse databases servers 20. Each one of the geographically diverse database servers is capable of communicating with the Institutional communications server 40. The database contains a plurality of user records 24. Each user record 24 has a plurality of data items 26. Illustrative examples of data items 26 include but are not limited to medical reports, blood tests, MRI images, x-rays, video and patient demographic information.

The database communications server 28 is in operational communication with the database server 20 and facilitates access to the information records by a user.

Preferable, each institutional communications server 40 is registered and authenticated for communications with the database communications server 28. This may be done by a combination of factors including but not limited to IP Address, MAC ID, authentication certificate, hardware key or other similar means. Each institutional communications server 40 may be considered to be a gateway between all of the institutions users, and the database communications server 28.

The communications channel 30 provides selective communication between the database communication server and the at least one institutional communications server 40. The communications channel 30 may be an internet connection, a private connection, or some other appropriate channel which can support the necessary bandwidth and security for the institutional communications server 40.

Each institution may have multiple user terminals 50, each in communication with the associated institutional communications server 40. Each user terminal 50 may include a display 56 and a data input device 58 such as a keyboard, mouse, touch screen, and the like.

In a preferred embodiment, each institution utilizes a user validation database 42. which is accessible by the institutional communication server. The user validation database 42 includes a plurality of user validation records 44. Each user validation record comprising a user photo, and associated facial recognition map of the user photo, and a numerical identifier corresponding to a radio frequency identification device 48.

In a preferred embodiment, each authorized user is issued an identification card 46. The identification card 46 includes a photograph of the face of the user and a radio frequency identification device 48 having a unique numerical identifier.

In still a further embodiment, as a user approached a user terminal 50, a camera 52 operationally coupled to the user terminal 50 captures a facial image of a user. Concurrently, a radio frequency identification interrogator 54 operationally coupled to the user terminal 50 interrogates the radio frequency identification device 48 coupled to the identification card 46. The user validation database 42 then compares the captured facial image and numerical identifier with the stored values. If the captured versions match the stored version the user is automatically logged onto the user terminal 50.

In even still a further embodiment the user terminal 50 logs off a user if the radio frequency identification device 48 associated with the user moves out of range of the radio frequency identification interrogator 54, or if the terminal 50 is inactive for a predetermined period of time. Additionally, the user may log off of the terminal 50 manually at any time.

In an embodiment the database communications server 28 provides user records 24 from the database when requested through the at least one user terminal 50 formatted as streaming video regardless of the format of the data item 26. The streaming video is ephemeral and does not leave a copy on the user terminal. This provides additional security of the record and improves compliance with the Health Insurance Portability and Accountability Act (HIPAA) requirements.

In at least one preferred embodiment, the system 10 also includes at least one insurer database server 60, a first insurer communications channel 64 and a second insurer communications channel 66. Typically, the insurer database server 60 is operationally coupled to an insurer authorization database 62. The insurer authorization database 62 facilitates pre-authorization of medical procedures based upon predetermine criteria. The first insurer communications channel 64 provides communication between at least one institutional communications server 40 and the insurer database server 60. The second insurer communications channel 66 provides communication between the database communication server and the insurer database server 60. A user is logged onto the user terminal 50 and is authenticated. The user then attempts to log into the insurer database server 60. The user is logged onto the insurer database server 60 after the insurer database server 60 receives authentication from the database communication server.

In a further preferred embodiment, the patient is authenticated prior to the insurer pre-authorizing the medical procedure. Illustrative examples of such medical procedures include, but are not limited to routine health-care visits with doctors, nurse practitioners, optometrists, dentists, chiropractors, filing prescriptions, procuring durable medical goods and the like. The patient authentication is done by matching information on an encoded identification card 46 issued to the patient by the insurer, and patient biometric information to information stored on the insurer database server 60. Illustrative examples of such biometric information include, but are not limited to: finger print, retinal scan, voice print, venous-arterial scan, facial recognition, etc. This type of authentication provides a counter-measure for medical billing fraud, as the identity of the patient, as well as the patients location at a specific time and place is validated prior to authorization of a medical procedure, In still a further preferred embodiment, the system 10, also includes a record owner terminal 38, a second communications channel 32, and a owner validation database. The record owner terminal 38 is associated with a record owner. Typically, the second communications channel 32 is a public channel, such as an internet connection. The owner validation database operationally coupled to the database communications server 28, and includes a plurality of owner validation records. Each owner validation record includes multi-facet authentication criteria for each record owner. Preferably, the multi-facet authentication criteria include at least two forms of authentication including retinal scan, voice print, venous-arterial scan, facial recognition, DNA, MAC ID, Domain Address, Email Address, telephone number, password, and authentication certificates.

In yet a further preferred embodiment a record owner may access at least one user record 24 associated with the record owner upon authentication of the record owner. The database communications server 28 provides the user record 24 in the original format of the data item 26 or as streaming video without regard to the original format of the data item 26 as the record owner may select.

In an embodiment the record owner may update, correct, or release at least a subset of the plurality of data items 26 associated with the record owner. Even for updated or corrected records, the original uncorrected or un-updated record is maintained and is accessible.

In still a further preferred embodiment, the system 10 also includes a translation database 72, and a translation engine 70. The translation database 72 includes a plurality of code reference records. Each one of the code reference records includes an associated medical code. Each one of the code reference records includes at least one associated narrative. The associated narrative may be in the owners primary language, such as English, French, Spanish, Chinese, American Sign Language and the like. The narrative is in basic terms, colloquially referred to as "plain English". The translation engine 70 is capable of operational communication with the database. The translation engine 70 systematically accesses the plurality of data items 26. The translation engine 70 is in operational communication with the translation database 72. The translation engine 70 creates associated narratives for any data item 26 with a corresponding associated medical code.

Additionally, the system 10 may also include an information record format translation engine 74. The information record format translation engine 74 converts a data item 26 to a streaming video format upon request from an authorized user.

In at least one embodiment, the system 10 also includes at least one wireless user terminal 78 and a third communications channel 34. The third communications channel 34 provides selective communication between the wireless user terminal 78 and the institutional communications server 40. The wireless user terminal 78 is authenticated through the use of multi-facet criteria similar to record owner authentication. An illustrative example of wireless user terminals 78 includes but is not limited to units used by emergency first responders such as emergency medical technicians, firemen, and police. Additional examples include terminals used in emergency rooms or for admissions purposes where bringing a terminal to a patient is beneficial.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

| Index of Elements for Information Record Management System | |
| --- | --- |
| 10. | Information Record Management System |
| 11. | |
| 12. | |
| 13. | |
| 14. | |
| 15. | |
| 16. | |
| 17. | |
| 18. | |
| 19. | |
| 20. | Database Server |
| 21. | |
| 22. | Database |
| 23. | |
| 24. | User Record |
| 25. | |
| 26. | Data item |
| 27. | |
| 28. | Database Communications Server |
| 29. | |
| 30. | Communications Channel |
| 31. | |
| 32. | Second Communications Channel |
| 33. | |
| 34. | Third Communications Channel |
| 35. | |
| 36. | |
| 37. | |
| 38. | Record Owner Terminal |
| 39. | |
| 40. | Institutional Communications Server |
| 41. | |
| 42. | User Validation Database |
| 43. | |
| 44. | User Validation Records |
| 45. | |
| 46. | Identification Cards |
| 47. | |
| 48. | Radio Frequency Identification Device |
| 49. | |
| 50. | User Terminal |
| 51. | |
| 52. | Camera |
| 53. | |
| 54. | RFID Interrogator |
| 55. | |
| 56. | Display |
| 57. | |
| 58. | Data Input Device |
| 59. | |
| 60. | Insurer Database Server |
| 61. | |
| 62. | Insurer Authorization Database |
| 63. | |

-continued

Index of Elements for Information Record Management System

| | | |
|---|---|---|
| 64. | First Insurer Communications Channel | |
| 65. | | |
| 66. | Second Insurer Communications Channel | |
| 67. | | |
| 68. | Record Owner Validation Database | |
| 69. | | |
| 70. | Translation Engine | |
| 71. | | |
| 72. | Translation Database | |
| 73. | | |
| 74. | Information Record Format Translation Engine | |
| 75. | | |
| 76. | | |
| 77. | | |
| 78. | Wireless User Terminal | |
| 79. | | |

I claim:

1. An information record management system comprising:

a records database operationally running on at least one database server computer, said database containing a plurality of user records, each user record have a plurality of data items;

a database communications server computer, said database communications server computer being in operational communication with said database server computer;

at least one institutional communications server computer, said at least one institutional server being registered and authenticated for communications with said database communications server computer;

a network communications channel, said network communications channel providing selective communication between said database communication server computer and said at least one institutional communications server computer;

at least one user terminal, said user terminal being in selective communication with said institutional communications server computer;

a user validation database, said user validation database being accessible by said institutional communication server computer, said user validation database having a plurality of user validation records, each user validation record comprising a user photo, and associated facial recognition map of said user photo, and a numerical identifier corresponding to a radio frequency identification device;

a plurality of radio frequency identification devices, each one of said plurality of radio frequency identification devices being associated with a specific user;

a camera operationally coupled to said at least one user terminal, said camera capturing a facial image of a user approaching said at least one user terminal;

a radio frequency identification interrogator operationally coupled to said at least one user terminal, said radio frequency identification interrogator interrogating at least one of said radio frequency identification devices operationally coupled to a user approaching said at least one user terminal;

wherein said at least one user terminal routes a paired facial image of an approaching user and a numerical identifier corresponding to a radio frequency identification device operationally coupled to an approaching user to said user validation database, if the paired facial image and numerical identifier match recorded values associated in said user validation database the associated user is automatically logged into the at least one institutional communications server computer for access to said database communications server computer;

wherein said at least one user terminal automatically logs off a user if said radio frequency identification device associated with the user moves out of range of said radio frequency identification interrogator;

wherein said database communications server computer provides user records from said database when requested through said at least one user terminal formatted as streaming video regardless of the format of a data item;

at least one record owner terminal, associated with a record owner;

a second network communications channel, said second communications channel being a public channel;

an owner validation database operationally coupled to said database communications server computer, said owner validation database having a plurality of owner validation records, each owner validation record including multi-facet authentication criteria for each record owner;

wherein a record owner may access at least one user record associated with the record owner upon authentication of the record owner, said database communications server computer providing said at least one user record in the original format of the data item or as streaming video without regard to the original format of the data item;

wherein the record owner may update, correct, or release at least a subset of the plurality of data items associated with the record owner;

a translation engine, said translation engine being in operational communication with said records database, said translation engine accessing at least one data item and generating a narrative based upon said data item, said data item being maintained, said narrative being operationally tagged to said data item.

2. The system of claim 1, wherein said database is replicated on a plurality of geographically diverse database communication servers, each one of said database communication servers being able to operationally communicate with any of the at least one institutional communication server computer.

3. The system of claim 2, wherein said multi-facet authentication criteria includes at least two criteria selected from the group of criteria consisting of finger print, retinal scan, voice print, venous-arterial scan, facial recognition, DNA, MAC ID, Domain address, email address, telephone number, password, and authentication certificate.

4. The system of claim 3, further comprising:

at least one insurer database server, said at least one insurer database server being operationally coupled to an insurer authorization database, said insurer authorization database facilitating pre-authorization of medical procedures based upon predetermined criteria;

a first insurer network communications channel, said first insurer communications channel providing communication between said at least one institutional communications server computer and said insurer database server;

a second insurer network communications channel, said second insurer communications channel providing communication between said database communication server and said insurer database server; and wherein a user is logged onto said at least one user terminal and is authenticated, the user then attempts to log into the insurer database server, said user being logged onto the insurer database server after said insurer database server receives authentication from said database communication server.

5. An information record management system comprising:
a records database operationally running on at least one database server computer, said database containing a plurality of user records, each user record have a plurality of data items;
a database communications server computer, said database communications server computer being in operational communication with said database server computer;
at least one institutional communications server computer, said at least one institutional server being registered and authenticated for communications with said database communications server computer;
a network communications channel, said network communications channel providing selective communication between said database communication server computer and said at least one institutional communications server computer;
at least one user terminal, said user terminal being in selective communication with said institutional communications server computer;
a user validation database, said user validation database being accessible by said institutional communication server computer, said user validation database having a plurality of user validation records, each user validation record comprising a user photo, and associated facial recognition map of said user photo, and a numerical identifier corresponding to a radio frequency identification device;
a plurality of radio frequency identification devices, each one of said plurality of radio frequency identification devices being associated with a specific user;
a camera operationally coupled to said at least one user terminal, said camera capturing a facial image of a user approaching said at least one user terminal;
a radio frequency identification interrogator operationally coupled to said at least one user terminal, said radio frequency identification interrogator interrogating at least one of said radio frequency identification devices operationally coupled to a user approaching said at least one user terminal;
wherein said at least one user terminal routes a paired facial image of an approaching user and a numerical identifier corresponding to a radio frequency identification device operationally coupled to an approaching user to said user validation database, if the paired facial image and numerical identifier match recorded values associated in said user validation database the associated user is automatically logged into the at least one institutional communications server computer for access to said database communications server computer;
wherein said at least one user terminal automatically logs off a user if said radio frequency identification device associated with the user moves out of range of said radio frequency identification interrogator;
wherein said database communications server computer provides user records from said database when requested through said at least one user terminal formatted as streaming video regardless of the format of a data item;
at least one insurer database server, said at least one insurer database server being operationally coupled to an insurer authorization database, said insurer authorization database facilitating pre-authorization of medical procedures based upon predetermined criteria;
a first insurer communications channel, said first insurer network communications channel providing communication between said at least one institutional communications server computer and said insurer database server;
a second insurer network communications channel, said second insurer communications channel providing communication between said database communication server and said insurer database server;
wherein a user is logged onto said at least one user terminal and is authenticated, the user then attempts to log into the insurer database server, said user being logged onto the insurer database server after said insurer database server receives authentication from said database communication server,
at least one record owner terminal, associated with a record owner;
a second network communications channel, said second communications channel being a public channel;
an owner validation database operationally coupled to said database communications server computer, said owner validation database having a plurality of owner validation records, each owner validation record including multi-facet authentication criteria for each record owner;
wherein a record owner may access at least one user record associated with the record owner upon authentication of the record owner, said database communications server computer providing said at least one user record in the original format of a data item or as streaming video without regard to the original format of the data item;
wherein the record owner may update, correct, or release at least a subset of the plurality of data items associated with the record owner;
a translation engine, said translation engine being in operational communication with said records database, said translation engine accessing at least one data item and generating an English narrative based upon said data item, said data item being maintained, said English narrative being operationally tagged to said data item; and
wherein the record owner is authenticated by said insurer database server through the use of an encoded identification card and owner biometric information matched to data stored on said insurer database server prior to pre-authorization of medical procedures based upon predetermined criteria, said biometric information selected from the group of biometric information types consisting of finger print, retinal scan, voice print, venous-arterial scan, and facial recognition.

6. An information record management system comprising:
a records database operationally running on at least one database server computer, said database containing a plurality of user records, each user record have a plurality of data items;
a database communications server computer, said database communications server computer being in operational communication with said database server computer;
at least one institutional communications server computer, said at least one institutional server being registered and authenticated for communications with said database communications server computer;
a network communications channel, said network communications channel providing selective communication between said database communication server computer and said at least one institutional communications server computer;
at least one user terminal, said user terminal being in selective communication with said institutional communications server computer;

a user validation database, said user validation database being accessible by said institutional communication server computer, said user validation database having a plurality of user validation records, each user validation record comprising a user photo, and associated facial recognition map of said user photo, and a numerical identifier corresponding to a radio frequency identification device;

a plurality of radio frequency identification devices, each one of said plurality of radio frequency identification devices being associated with a specific user;

a camera operationally coupled to said at least one user terminal, said camera capturing a facial image of a user approaching said at least one user terminal;

a radio frequency identification interrogator operationally coupled to said at least one user terminal, said radio frequency identification interrogator interrogating at least one of said radio frequency identification devices operationally coupled to a user approaching said at least one user terminal;

wherein said at least one user terminal routes a paired facial image of an approaching user and a numerical identifier corresponding to a radio frequency identification device operationally coupled to an approaching user to said user validation database, if the paired facial image and numerical identifier match recorded values associated in said user validation database the associated user is automatically logged into the at least one institutional communications server computer for access to said database communications server computer;

wherein said at least one user terminal automatically logs off a user if said radio frequency identification device associated with the user moves out of range of said radio frequency identification interrogator;

wherein said database communications server computer provides user records from said database when requested through said at least one user terminal formatted as streaming video regardless of the format of a data item;

at least one insurer database server, said at least one insurer database server being operationally coupled to an insurer authorization database, said insurer authorization database facilitating pre-authorization of medical procedures based upon predetermined criteria;

a first insurer network communications channel, said first insurer communications channel providing communication between said at least one institutional communications server computer and said insurer database server;

a second insurer network communications channel, said second insurer communications channel providing communication between said database communication server and said insurer database server;

wherein a user is logged onto said at least one user terminal and is authenticated, the user then attempts to log into the insurer database server, said user being logged onto the insurer database server after said insurer database server receives authentication from said database communication server computer, at least one record owner terminal, associated with a record owner;

a second network communications channel, said second communications channel being a public channel;

an owner validation database operationally coupled to said database communications server computer, said owner validation database having a plurality of owner validation records, each owner validation record including multi-facet authentication criteria for each record owner;

wherein a record owner may access at least one user record associated with the record owner upon authentication of the record owner, said database communications server computer providing said at least one user record in the original format of the data item or as streaming video without regard to the original format of the data item wherein the record owner may update, correct, or release at least a subset of the plurality of data items associated with the record owner;

a translation database, said translation database having a plurality of code reference records, each one of said code reference records having an associated medical code, each one of said code reference records having at least one associated English narrative;

a translation engine, said translation engine being in operational communication with said records database, said translation engine systematically accessing said plurality of data items, said translation engine being in operational communication with said translation database, said translation engine creating associated English narratives for any data item with a corresponding associated medical code;

an information record format translation engine, said information record format translation engine converting a data item to a streaming video format upon request from an authorized user;

a wireless user terminal;

a third network communications channel, said third communications channel having a wireless component; said third communications channel providing selective communication between said institutional communications server computer and said wireless user terminal; and wherein the record owner is authenticated by said insurer database server through the use of an encoded identification card and owner biometric information matched to data stored on said insurer database server prior to pre-authorization of medical procedures based upon predetermined criteria, said biometric information selected from the group of biometric information types consisting of finger print, retinal scan, voice print, venous-arterial scan, and facial recognition.

7. The system of claim 6, wherein said wireless user terminal is a communications terminal for first responders.

8. The system of claim 6, wherein said wireless user terminal is a communications terminal for emergency room use.

9. The system of claim 6, wherein said wireless user terminal is a communications terminal for admissions use.

* * * * *